United States Patent [19]

McCormick

[11] Patent Number: 4,569,647

[45] Date of Patent: Feb. 11, 1986

[54] APPARATUS FOR PREPARING AND EMBEDDING TISSUE SAMPLES FOR HISTOLOGICAL EXAMINATION

[75] Inventor: James B. McCormick, Chicago, Ill.

[73] Assignee: Pelam, Inc., Chicago, Ill.

[21] Appl. No.: 533,192

[22] Filed: Sep. 16, 1983

[51] Int. Cl.[4] .............................................. B29C 41/00
[52] U.S. Cl. .................................. 425/117; 118/429; 118/500; 249/81; 249/126; 422/99; 425/121; 425/470; 435/284; 435/287
[58] Field of Search ................ 425/84, 116, 117, 121, 425/470; 249/81, 91, 113, 126, 133, 160; 83/915.5; 264/78, 158; 134/12; 203/DIG. 16, 60; 118/429, 500; 422/99, 102; 435/284, 287, 300, 301

[56] References Cited

U.S. PATENT DOCUMENTS

| | | | |
|---|---|---|---|
| 2,996,762 | 8/1961 | McCormick | 18/26 |
| 3,128,902 | 4/1964 | Barnum | 435/284 |
| 3,319,289 | 5/1967 | McCormick | 18/5 |
| 3,456,300 | 7/1969 | Pickett | 425/117 |
| 3,527,837 | 9/1970 | Woerner et al. | 203/60 |
| 3,674,396 | 7/1972 | McCormick | 425/117 |
| 3,772,158 | 11/1973 | Sarno | 203/60 |
| 3,847,755 | 11/1974 | Chanel et al. | 203/60 |
| 3,884,769 | 5/1975 | Mikitenko et al. | 203/60 |
| 4,224,110 | 9/1980 | McCord | 203/DIG. 16 |
| 4,321,330 | 3/1982 | Baker et al. | 435/284 |
| 4,352,888 | 10/1982 | Tisbo et al. | 435/287 |

Primary Examiner—Jay H. Woo
Assistant Examiner—Timothy W. Heitbrink
Attorney, Agent, or Firm—Fitch, Even, Tabin & Flannery

[57] ABSTRACT

Capsules in which histological tissue samples are prepared for embedding and in which the samples are embedded include a first and a second member, at least one of the members including a frame that defines an opening. The members have complementary surfaces for establishing peripheral contact between the members around the opening. A porous material is spread across the opening so that when the members are in peripheral contact with each other, a tissue-holding region is defined inward of the porous material. The porous material has a porosity that accesses processing liquids and liquified embedding material, such as molten paraffin, but prevents stray parts of the tissue from floating free of the region. Preferably, the second members also comprise a frame defining a second opening and porous material spread across the second opening. Preferably, the capsules having openings in both members are stackable in sealing relationship with one another to provide a central passageway through which processing liquids and liquified embedding material may be passed, thereby permitting simultaneous processing of a plurality of tissue samples. Preferably, one of the frames, that has an opening covered by a porous material, is adapted to retain a protruding block of solidified embedding material having the tissue sample held outward so that the one frame may be clamped in a microtome chuck and tissue slices shaved from the protruding embedding material.

9 Claims, 8 Drawing Figures

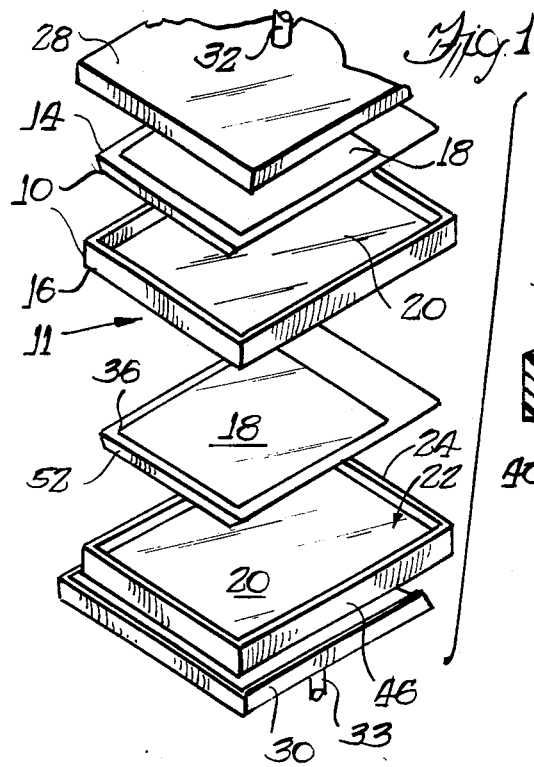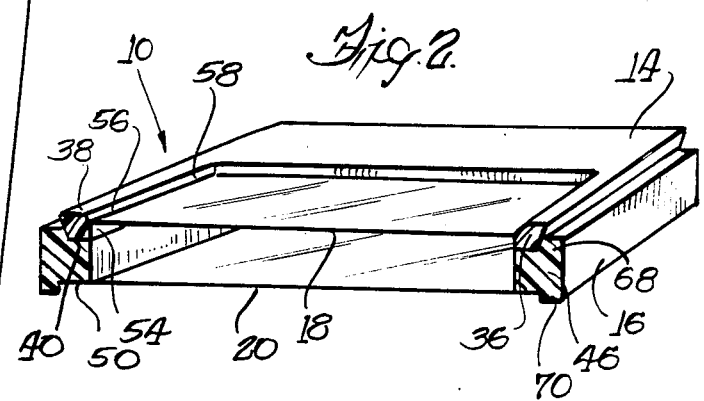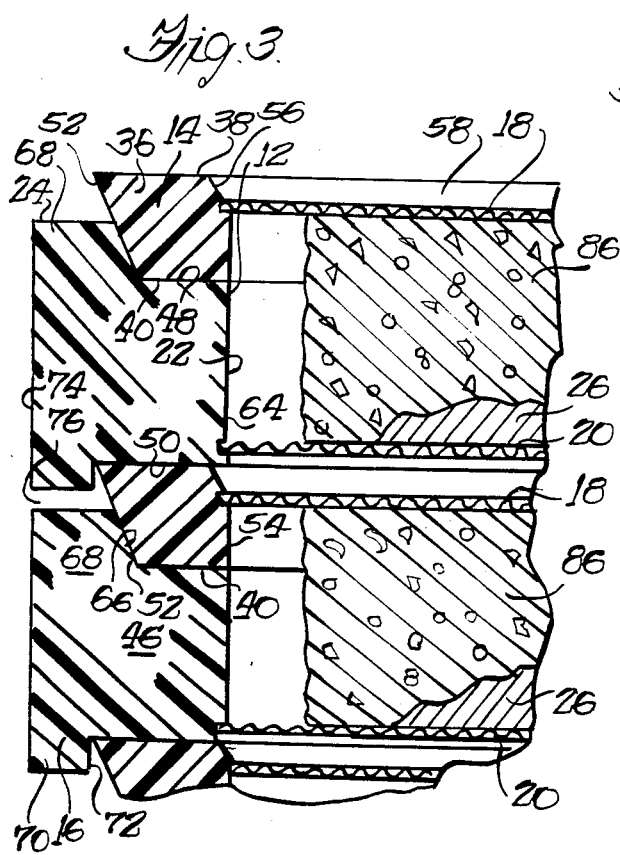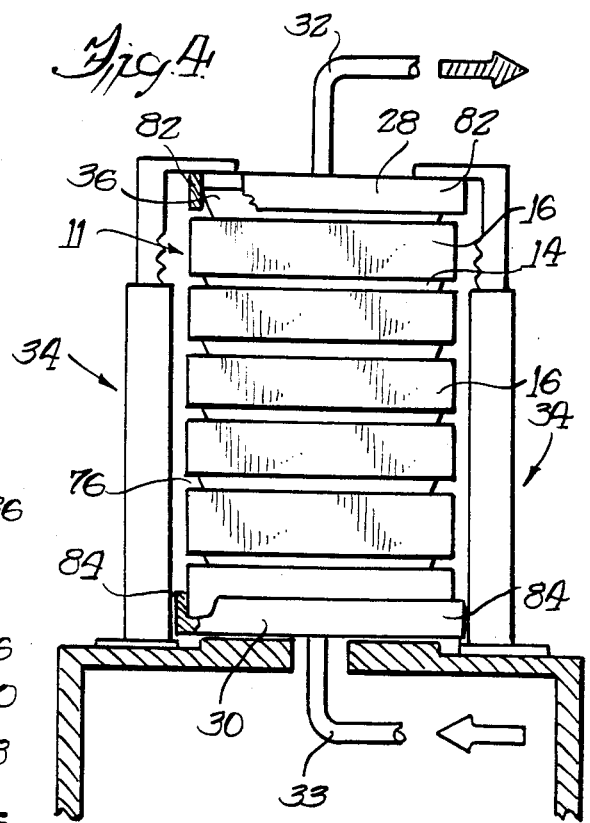

APPARATUS FOR PREPARING AND EMBEDDING TISSUE SAMPLES FOR HISTOLOGICAL EXAMINATION

The present invention relates to the preparation of tissues for histological examination and more particularly to improved methods and apparatus for embedding tissue in paraffin or the like preparatory to microscopic examination.

BACKGROUND OF THE INVENTION

It is a standard procedure to prepare tissue samples for microscopic examination by embedding the tissue in paraffin and slicing the paraffin-embedded tissue very thinly with a microtome. Preparatory to embedding, the tissue is pretreated in various solutions appropriate to its examination. Typically, prior to paraffin embedding, the tissue sample is fixed, dehydrated, cleared, infiltrated with molten paraffin and, depending on the test, stained.

A histology laboratory daily receives a large number of tissue samples for examination, and it is important that the tissues be prepared as efficiently as possible. Described in my U.S. Pat. No. 3,674,396 are capsules in which a tissue sample is both prepared for embedding through exposure to various solutions and then embedded within a capsule. In these capsules, perforated walls are used to retain the tissues while accessing to the tissue the various solutions and, finally, molten paraffin. The perforations are of a minimal size; any substantial reduction in perforation size would reduce the efficiency of tissue processing and would be inappropriate for molding by current technology.

Typically, the tissue sample for examination is a unitary, connected portion of tissue; however, small parts of the tissue sample may be dislocated during tissue processing. Alternatively, the biopsy may be performed on minute fragments less than about 0.1 mm. in diameter, such as bronchial washings, cytology preparations and aspiration biopsies which may be gathered by the new skinny needles. If several tissue capsules are processed together, the processing solutions may carry these broken-away tissue particles or "floaters" from one sample to another. The transfer of even very minute particles of tissue from one sample to another may result in misleading diagnoses, particularly where the object of the examinations is to detect invasion of tissue by foreign cells, e.g., to determine whether a tumor has metastased.

It is a primary object of the present invention to provide apparatus for processing and embedding tissue samples at maximum efficiency and without cross-contamination from one sample to another. Other objects of the invention include providing continuous flow systems for tissue-processing liquids which recycle the various reagents that are used for processing the tissue, and in the economical use of processing capsule components in the end stage of tissue embedding and slicing.

SUMMARY OF THE INVENTION

Capsules for processing and embedding tissue samples each include a mold, which provides a cavity to receive a tissue sample, having an open upper end and a porous or non-porous bottom. The capsule further includes a cover which fits over the open upper end of the mold. The cover comprises a frame on which is located a web of porous material intermediate the top and bottom of the frame so that the cover is provided with a recess. The porous web provides access to tissue processing liquids and liquid tissue embedding material, such as paraffin, but prevents passage of tissue floaters, thereby preventing cross-contamination of individually capsuled, jointly processed tissue samples. The cover recess above the porous web is at least partially filled with liquified tissue embedding material so that when the embedding material solidifies, e.g., by cooling, the porous web is embedded and the solidified material is thereby formed into a block in the mold. With the porous web and tissue sample mutually embedded in the block of solidified material, the block is removed from the mold, and the cover may be clamped in a microtome chuck with the embedded tissue exposed for slicing by a microtome blade.

In a preferred embodiment, the capsules are adapted to be stacked, and the molds are provided with porous bottoms that do not adhere to the embedding material, particularly paraffin. The stacked capsules provide a passageway running from top to bottom, defined by the molds and cover frames. The tissues held within the stacked capsules are processed by flowing solutions through the passageway formed by the stacked capsules and finally introducing liquid embedding material into the stacked capsules. When the stack is separated, each tissue sample is embedded in a block of material that is attached to the respective covers.

Efficient tissue processing and embedding is provided by a continuous flow system, including distillation units to recover solvents that are used to process the tissue samples. In order to dehydrate the tissues without substantial damage to tissues, a unique solvent mixing system is used to initially provide a mixture of a diluent, such as water, and dehydrating solvent, e.g., ethanol, to the tissue and gradually and continuously change the composition of the mixture to pure dehydrating solvent.

BRIEF DESCRIPTION OF THE DRAWINGS

FIG. 1 is an exploded perspective view of a stack of capsules embodying various features of the present invention;

FIG. 2 is a perspective view of a capsule of FIG. 1, partially in section;

FIG. 3 is partial cross-sectional view of a stack of capsules having tissue samples contained therein;

FIG. 4 is a side elevational view, partially in section, of a clamped stack of tissue capsules;

DETAILED DESCRIPTION OF THE PREFERRED EMBODIMENT

Figure 5:
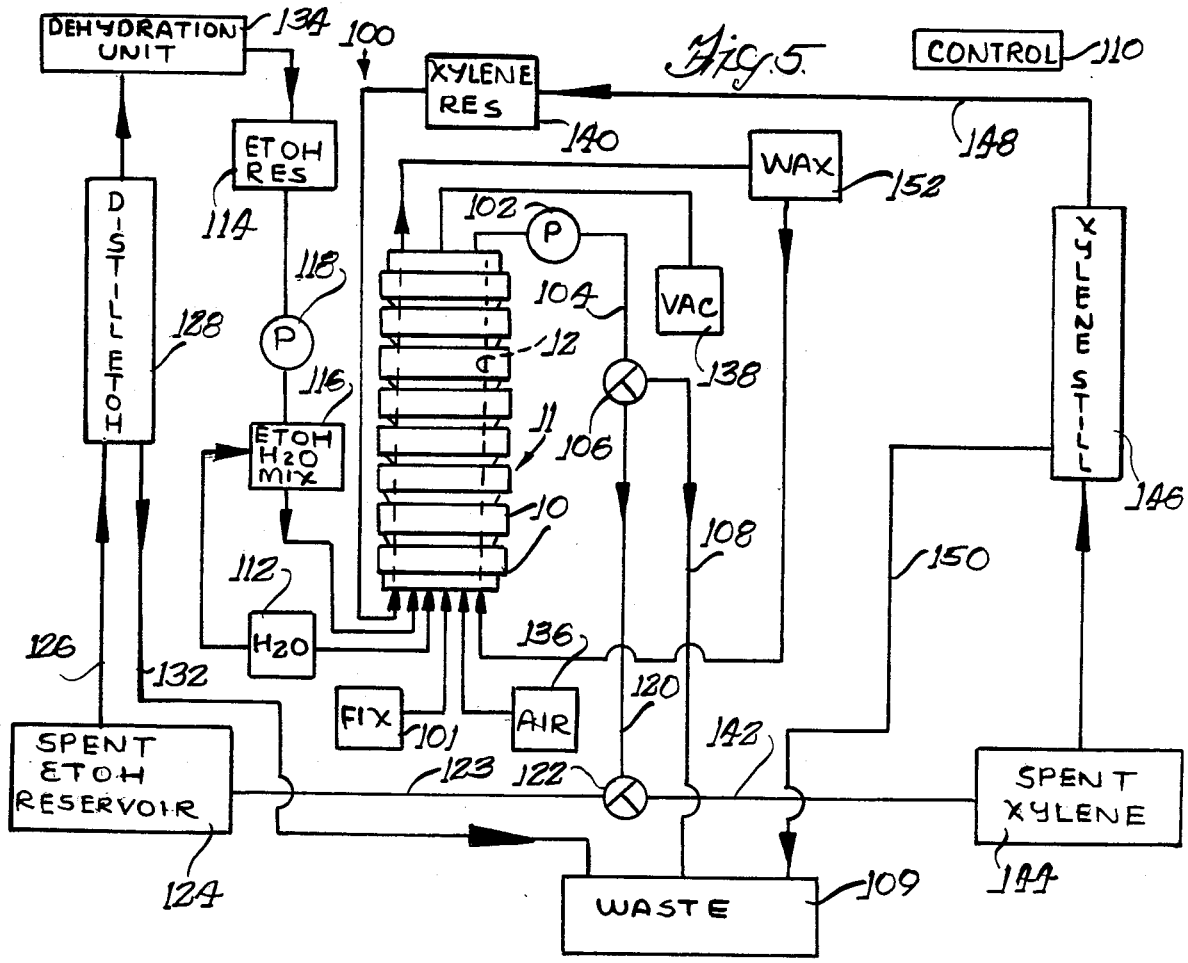
FIG. 5 is a block diagram of a system for delivering processing liquids to a stack of tissue capsules and apparatus for recovering and recycling processing liquids.

Illustrated in FIG. 1 is a plurality of two-part tissue capsules 10 which represent a preferred embodiment of the present invention and which may be piled into a continuous stack 11 to provide for processing and embedding of several tissue samples. When stacked together, the capsules 10 collectively define a continuous interior passageway 12 (FIG. 3) through which processing solutions and liquid embedding material may be conducted. Each capsule 10 comprises a cover 14 and a mold 16, the cover and mold each framing a porous material 18, 20 through which liquids, but not tissue, may pass. Each mold has a cavity 22 in which is disposed a tissue sample 26 (FIG. 3). The capsules 10 are adapted to mate with each other and when compressed together seal peripherally with the molds or covers stacked above and below, the covers thereby closing off the cavities 22 of the next lower molds.

An upper plate 28 and a lower plate 30 complete the stack 11, closing off the ends of the passageway 12. Each plate 28, 30 has a centrally located conduit 32, 33 providing for liquid passage through the interior passageway 12. The upper plate 28 and lower plate 30 are pressed toward each other by a ratchet clamp assembly 34, compressing the capsules 10 into sealing peripheral contact with each other.

Each cover 14 comprises a generally rectangular frame 36 molded from a relatively rigid polymeric material, such as Delrin acetal, and the porous material 18 is spread within the frame about midway between a flat upper surface 38 and a flat lower surface 40 of the frame. One side section of the frame 36 is wider than the others providing a labeling surface area. The frame 36 is shaped for mating, sealing peripheral contact with molds 16, above and below, and later processing, discussed hereinafter. The flat upper and lower surfaces 38, 40 contact, respectively, a flat lower surface 50 of the mold 16 thereabove and a flat upper surface 48 of the mold therebelow. The outside surfaces 52 of the cover 14 are flared outward from the lower surface 40 to the upper surface 38. The porous material 18 is fixed into the cover frame 36 intermediate the upper surface 38 and lower surface 40 of the frame. Below the porous material or web 18, the interior surfaces 54 of the frame 36 are vertical; however, above the porous material 18 the interior surfaces 56 flare outwardly to the upper surface 38.

The porous material 18 is attached to the frame, preferably by molding but alternatively by welding, gluing etc. into the frame 36. The porous material 18 is a porous fabric, preferably non-woven, which readily passes liquids but retains any floating tissue. It also has considerable tear strength because the solidified embedding material is held to the cover primarily by means of the fabric. The fabric preferably has a porosity between about 35% and about 65% with a maximum pore size of about 5 microns. A preferred web is non-woven nylon, such as that sold under the trademark Cerex by Monsanto.

The mold 16 is adapted for holding the tissue sample 26, for defining the shape of a block 60 of solidified embedding material, such as paraffin, that is subjected to the microtome 62 (FIG. 7) and for sealing with covers 14 in a stack. Furthermore, the mold 16 is adapted to be easily separated from a hardened block 60 so that the block remains attached to the cover 14 rather than to the mold 16. The material from which the mold frame 46 is formed is softer than the material of which the cover frame 36 is formed and is resilient. The resiliency of the mold frame 46 permits it to deform slightly under compression, as when the stacked covers 14 and molds 16 are held within the ratchet clamp assembly 34, and helps to assure good peripheral sealing with the cover frames 36 above and below. The deformation caused by compression is reversed after the stack 11 is released from the clamp assembly 34, causing each mold 16 to free itself from the solidified paraffin block 60. A suitable material for forming the mold frame 46 is low density polyethylene.

The interior surfaces 64 of the generally rectangular mold frame 46 are vertical and generally continuous with the vertical lower interior surfaces 54 of the cover frames 36. The interior surfaces 64 define the edges of the embedding material block 64. The flat lower surface 50 of the mold frame 46 provides peripheral sealing with the flat upper surface 38 of the next lower cover frame 36. The flat upper surface 48 of the mold frame 46 is matched to the flat lower surface 40 of the cover frame 36; however, primary peripheral sealing between the mold frame and the next higher cover frame is between the flared outer surfaces 52 of the cover frame and correspondingly flared interior surfaces 66 of an upstanding peripheral flange 68 of the mold frame 46. The mold frame 46 also has a depending peripheral flange 70 with vertical interior surfaces 72 proportioned to closely surround the upper end of the next lower cover 14. The outside surfaces 74 of the mold frame 46 are vertical and continuous through the upstanding and depending peripheral flanges 68, 70. The vertical dimensions of the upstanding and depending peripheral flanges 68, 70 are less than the height of the cover frame 36 so that when the molds 10 and covers 14 are stacked together, indentations 76 are left between adjacent molds, facilitating eventual separation of the molds and covers.

The porous mold material 20 at the bottom of the mold 16 is fixed to the mold frame 16. The porous material 20 may be similar to the cover porous material 18, permitting fluid to flow through the interior passageway 12 but retaining any floating tissue particles; however, the mold porous material separates on the cleavage plane of its upper surface because of the more flexible material to which it is affixed so that the solidified paraffin block 60 separates easily therefrom.

The porous material 20 is attached to the mold frame 46 closely adjacent to its lower end and tautly spread thereacross. Tension in the porous material 20 assures that it remains flat so that the paraffin block 60 has a flat front face (FIG. 6) appropriate for slicing.

The upper plate 28 and lower plate 30 are flat members of relatively rigid material, each having a peripheral lip 82, 84 for receiving, respectively, the upper end of the uppermost cover 14 and the lower end of the lowermost mold 16. The plates 28, 30, particularly the upper plate, may have an interior gasket (not shown), for sealing with the mated member. The conduits 32, 33 of the upper plate 28 and lower plate 30 lead into centered openings through these plates.

Tissue samples 26 are placed in the molds 16. It is intended that the tissue samples 26 remain immobilized in the molds 16 in an orientation most appropriate for microtome slicing, and generally, an insert 86 of a spongy material, such as low-density polyurethane, is placed over each tissue sample. The labeling area of the cover frame 30 is marked, and the cover 14 is loosely applied to the mold 16 to complete the capsule 10. A plurality of capsules 10 are stacked together and sandwiched between the upper plate 28 and lower plate 30. The upper and lower plates are then clamped and ratcheted, compressing the stack 11 and deforming the molds 16 slightly to seal tightly with the adjacent covers 14. As the stack 11 is compressed, the sponge material inserts 86 are also compressed between the porous material webs 18, 20 of each capsule 10 holding the tissue samples 26 firmly against the bottoms of the molds 16. An alternative method of positioning the tissue is to soak the tissue sample in a thin molten gelatin or similar protein material before placing the sample on the mold porous material 20. When the gelatin solidifies, it adheres the sample to the porous material where it remains throughout processing and embedding.

The port conduits 32, 33 are then connected to a liquid flow system, indicated generally at 100 (FIG. 5). Various processing solutions, including fixing solutions, dehydrating solutions and clearing solutions, are successively introduced. Flow through the passageway 12 in the stack 11 of capsules 10 may be by gravity, but preferably, the solutions are pumped through the stack under pressure. After the tissue samples 26 have been processed, liquified embedding material, such as molten paraffin, is introduced into the stack. Generally, a vacuum is applied to the molten paraffin in the passageway 12 for the purpose of forcing the paraffin into the interstices of the tissue samples. Sufficient molten paraffin is added to fill the entire interior passageway 12 of the stack 11. The paraffin is allowed to solidify (this process may be hastened by removing the stack to a cooling unit), and then the stack 11 is unclamped and the capsules 10 separated. When the covers 14 and molds 16 are separated, the paraffin blocks 60 are each adhered to the cover porous material 18 and held in the flared upper region 58 of the cover frames 36. On the other hand, the paraffin blocks 60 separate easily from the resilient molds frames 46 as well as from the treated or selected mold porous material 20. As a result, the blocks 60 of paraffin are held by the covers 16, each block having an outwardly protruding portion 87 that contains the tissue sample 26. The cover frame 36 is clampable in a spring- or clamp-activated microtome chuck 89, and the protruding portion 87 of the block 60 is sliced with a microtome 62 in a conventional manner.

The stacked capsules 10 are particularly adapted for tissue processing and embedding in a continuous flow system 100 (FIG. 5) that automatically provides various liquids through the interior passageway 12. The automated flow system, for the sake of simplicity, does not show all of the pumps and valves which are necessary for the operation of the system and is illustrated in block diagram form.

The capsules 10 are filled with tissue samples 26, stacked and clamped as described above. (The liquids are shown as being directed upwardly through the stack 11; however, the liquids might also be directed downwardly through the stack passageway 12.) Thereupon, a fixative, such as formalin (formaldehyde mixed to a 10% solution with water), is pumped from a fix reservoir 101 into the stack 11 and maintained therein for a sufficient time to fix the tissues. (Alternatively, the tissues could be fixed prior to their insertion into the capsules 10.) A pump 102 is activated in a line 104 leading from the upper end of the stack to remove fixative from the stack 11, and the formalin is directed through a three-way valve 106, through a line 108 to a waste reservoir 109. The pump 102, valve 106, and other valves and pumps of the system 100 are controlled by a central control unit 110, such as a commercially available microprocessor. The fixative is then rinsed from the stack with water, the spent water being pumped through the waste line 108.

Subsequent to fixation and rinsing, the tissue samples 26 are dehydrated, e.g., with ethanol. Because a sudden shift from a water environment to an ethanol environment would generally result in shock to the tissue samples, distorting their appearance and rendering them generally unsuitable for histological examination, the system 100 provides exposing the tissue samples to liquid that changes gradually and continuously from a water-ethanol mixture to pure ethanol. Water from the source 112 and ethanol from an absolute ethanol reservoir 114 are introduced into a mixing chamber 116 in an initial mix which will generally range from about 50 to about 100 volume percent water, and this mixture is drawn through the stack 11 by the pump 102. A gradual and consistent change in ethanol concentration to 100 percent ethanol is achieved by continuously replacing solution withdrawn from the mixing chamber 116 with pure ethanol from the ethanol reservoir 114. By matching the rate of a pump 118 supplying ethanol from the reservoir 114 to the mixing chamber 116 to the rate of the pump 102 drawing liquid from the chamber through the stack 11, the volume of the ethanol-water mixture in the mixing chamber is kept constant. The concentration of ethanol in the mixing chamber 116 at any time can be calculated by the formula:

$$C = x - (x-z)e^{v-yt}$$

where
y = ml/min ethanol being added
x = concentration of ethanol
z = concentration of ethanol in original volume
V = original volume
C = concentration of ethanol in maintained volume at time "t"

After the ethanol in the mixing chamber 116 has reached a certain concentration, e.g., above about 95 volume percent, the ethanol-water mixture is allowed to empty from the mixing chamber 116, and 100% ethanol is pumped through the stack 11. The absolute ethanol is passed through the stack for a sufficient time to insure substantially complete dehydration of the tissue samples 26.

During tissue dehydration, the three-way valve 106 is activated to direct the water-alcohol mixtures through line 120 to another three-way valve 122 which directs the solvent through line 123 to a spent ethanol reservoir 124. From the spent ethanol reservoir 121, the solution is withdrawn through line 126 to a distillation unit 128 which directs substantially pure ethanol through line 130 and water through line 132 to waste 109. The distillation unit 128 has temperature sensors that are connected to microprocessors in the control unit for controlling the distillation according to physical optima to obtain maximum recovery. Because ethanol and water form an azeotrope at about 95% ethanol, the substantially pure ethanol is passed through a dehydration unit 134 which removes residual water from the ethanol before the ethanol is returned to the absolute ethanol reservoir 114.

Upon completion of dehydration, pressurized air from source 136 is introduced into the stack 11 to force liquid from the stack, and then the stack is subjected to a vacuum 38 to evaporate residual ethanol. Then, pure xylene from a reservoir 140 is passed through the stack 11 to clear the tissues. The xylene that is pumped through the stacks 11 is directed with valve 106 through line 120 and by three-way valve 122 through line 142 to a spent xylene reservoir 144. The spent xylene from reservoir 144 is purified in a second distillation unit 146 before being returned through line 148 to the xylene reservoir 140. (Alternatively, the same distillation unit might be used for both xylene and ethanol distillation using a cycle with different temperature and switching parameters.) Residual liquids are directed from the distillation unit 146 through line 150 to waste.

After the xylene has been passed through the stack 11, the stack is again flushed with air and then opened to the vacuum 138 in an attempt to remove as much solvent as possible. Next, molten paraffin from reservoir 152 is introduced into the stack 11, and the stack is communicated to the vacuum 138 which causes the paraffin to infiltrate into the tissues. Additional paraffin is introduced into the stack to fill any void regions within the passageway 12, and the paraffin is allowed to solidify. In most cases, the paraffin that infiltrates the tissue is the same as the embedding material; however, in some cases a more free-flowing paraffin may be used for tissue infiltration and a paraffin of improved cutting quality used for embedding the material.

As the paraffin hardens in the passageway 12, the processing apparatus is reconnected to further stacks of capsules 10, and the process is repeated. In this manner, numerous tissue samples 26 are automatically prepared and embedded, permitting the major portion of the technician's time to be spent with other work. The system provides for recovery of about 90 percent of the ethanol and xylene used in each cycle, thereby minimizing solvent useage as well as reducing solvent contamination of the immediate environment.

Figures 6, 7, 8:
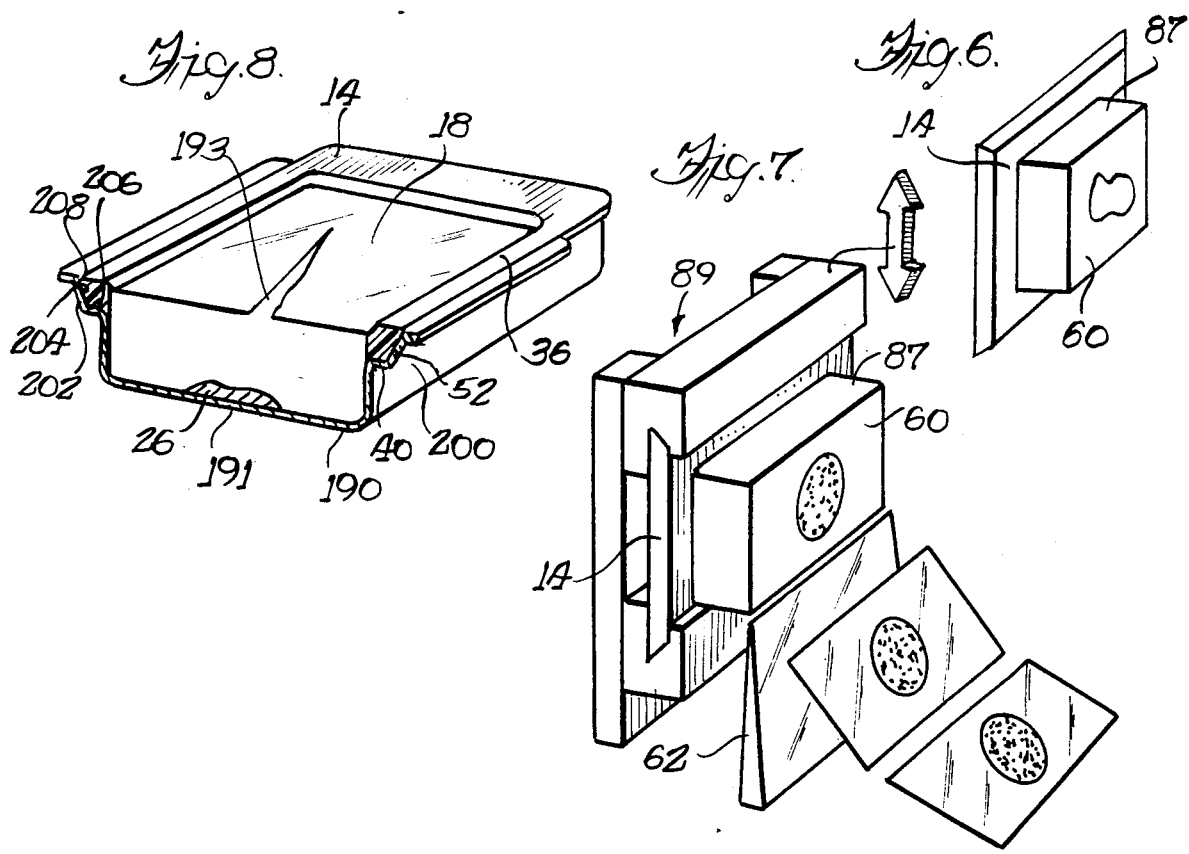
FIG. 6 is a perspective view of a cover for the tissue capsules with a tissue-containing block embedded.
FIG. 7 is a perspective view of the cover and block of FIG. 6 clamped in a chuck for cutting by a microtome blade.
FIG. 8 is a perspective view, partially in section, of the cover of the tissue capsule used to as a cover of a pan in which the tissue is placed for embedding subsequent to processing.

In some cases, it may be desirable to process special or difficult to orientate tissue samples in a stack but embed the tissue samples individually. Illustrated in FIG. 8 is an illustration of an individual embedding mold 190 adapted to receive the capsule cover 14 as its cover. The mold 190 comprises a rectangular pan with a flat base 191 and slightly flared upstanding sidewalls 200. A rim portion 202 extends outward of the upper end of the sidewalls 200 and provides a recess 204 with a flat upwardly-facing surface 206 and inclined side surfaces 208 that are matched to the lower surface 40 and inclined exterior surfaces 52 of the cover 14 so as to receive the cover in a close fit.

The tissue sample 26 is processed as described above and, while still in the stack 11, vacuum-impregnated with embedding material. However, instead of being allowed to solidify, excess embedding material is drained from the stack, and the tissue sample 26 is removed from its capsule 10 and oriented on the base 191 of the mold 190. Then the mold 190, which is preferably made of metal, is placed on a cooling block (not shown) to fix the tissue sample 26 in place.

Prior to placing the cover 16 on the mold 190, the porous material 18 is preferably slit at 193 to provide access by molten embedding material. Molten embedding material is poured into the mold 190 to above the level of the slit porous material 18 so that the porous material is embedded in the block 60 that forms when the poured embedding material solidifies, thereby affixing the block to the cover 14.

Several advantages of the present invention may now be more fully appreciated. The capsules in which the tissue samples are completely processed, from fixation through embedding, are simple and inexpensive. The capsules assure adequate flow-through of processing liquids while providing substantially complete assurance against cross-contamination of tissue samples processed in the same solutions. The tissue can be prearranged within the capsules so that they are embedded with respect to the plane of microtome cutting in the orientation which best facilitates their examination. After embedding, the covers of the capsules are suitable for direct placement in a microtome chuck with the tissue-containing paraffin blocks exposed for microtome slicing. The capsules that are stackable provide for processing the tissues with minimal volumes of solutions and for embedding with a minimal volume of paraffin. The liquid flow system, to which the stacked tissue capsules are particularly adaptable, is automatic and continuously operable, requiring almost no technician time. The system efficiently uses solvents by recovering the same, a feature which also substantially reduces solvent contamination of the environment. The liquid flow system also incorporates the means to gradually and continuously change the environment of the tissue from water to dehydrating solvent so that dehydration leaves the tissue in excellent condition for subsequent examination.

While the invention has been described in terms of certain preferred embodiments, modifications obvious to one with ordinary skill in the art may be made without departing from the scope of the invention. For example, the automatic solvent system has been described in terms of a standard protocol; however, the system may be modified to utilize solvents necessary to perform other tissue preparation protocols known in the art. Where desired, the tissue samples may be stained within the capsules.

Various features of the invention are recited in the following claims.

What is claimed is:

1. Apparatus for the simultaneous preparation of multiple tissue specimens for histological examination comprising
   a plurality of cooperating stackable capsules, each of said capsules including a mold member and a complementary removable cover member,
   said mold member including an open mold frame formed from a material that is resilient and deformable under compression, said cover member including an open cover frame formed from a material that is more rigid than said mold frame, the interior sidewalls of said mold frames and said cover frames in a stack of capsules defining a continuous fluid passageway for tissue treating fluids,
   said mold member including a porous web spanning said fluid passageway, said cover member including a porous web spanning said passageway, said webs in each of said capsules being spaced apart defining therebetween a tissue-receiving cavity.

2. Apparatus in accordance with claim 1 wherein said mold frame has a recessed seat formed in its upper surface adapted to receive and support said cover frame.

3. Apparatus in accordance with claim 1 including means to compress a stack of capsules.

4. Apparatus in accordance with claim 3 including upper and lower cover plates in sealing engagement with the uppermost cover member and lowermost mold member, and means for introducing tissue-treating fluids into said fluid passageway.

5. Apparatus in accordance with claim 3 including means for introducing, successively or concurrently, a plurality of tissue-treating fluids into said fluid passageway and means for collecting spent fluids from said fluid passageway.

6. Apparatus in accordance with claim 5 including mixing means for said tissue-treating fluids, said fluids including water and a miscible dehydrating solvent and control means for controlling the solvent concentration in the water-solvent mixture.

7. Apparatus in accordance with claim 5 including means to recover solvent from the spent water-solvent mixture.

8. Apparatus in accordance with claim 1 wherein the porous web has a porosity of between about 35 and about 65 percent and a maximum pore size of about 5 microns.

9. Apparatus in accordance with claim 8 wherein the porous web is nonwoven nylon.

* * * * *

UNITED STATES PATENT AND TRADEMARK OFFICE
CERTIFICATE OF CORRECTION

PATENT NO. : 4,569,647
DATED : February 11, 1986
INVENTOR(S) : James B. McCormick It is certified that error appears in the above-identified patent and that said Letters Patent is hereby corrected as shown below:

Column 6, line 26 (page 10, line 32) should read:

$$C = x - (x-z)e^{\frac{-yt}{v}}$$

Signed and Sealed this

Twenty-fourth Day of June 1986

[SEAL]

Attest:

DONALD J. QUIGG

Attesting Officer

Commissioner of Patents and Trademarks